United States Patent [19]

Kelly

[11] Patent Number: 4,964,412
[45] Date of Patent: Oct. 23, 1990

[54] DIAGNOSTIC METHOD FOR DERMATURE TESTING

[76] Inventor: Kevin G. Kelly, 152 Mannamead Road, Hartley, Plymouth Devon Pl3 5QL, United Kingdom

[21] Appl. No.: 220,153

[22] Filed: Jul. 18, 1988

[30] Foreign Application Priority Data

Jul. 17, 1987 [GB] United Kingdom ............... 8716955

[51] Int. Cl.$^5$ ............................................. A61B 19/00
[52] U.S. Cl. ..................................... 128/740; 128/744
[58] Field of Search ................................ 128/740, 744

[56] References Cited

U.S. PATENT DOCUMENTS

| 2,704,539 | 3/1955 | Fisher ................................. 128/744 |
| 2,744,520 | 5/1956 | Torricelli ........................... 128/740 |
| 3,662,744 | 5/1972 | Low et al. ......................... 128/744 |
| 3,933,148 | 1/1976 | Wyler et al. ...................... 128/744 |

*Primary Examiner*—Max Hindenburg
*Attorney, Agent, or Firm*—Cushman, Darby & Cushman

[57] ABSTRACT

A dermatome testing instrument comprises a barrel member with a resiliently biassed probe member carried therein and extending as one end. The probe member is formed as a rounded point at its tip so that, in use, precise investigation of dermatomes without causing undue discomfort to the patient.

1 Claim, 1 Drawing Sheet

DIAGNOSTIC METHOD FOR DERMATURE TESTING

BACKGROUND OF THE INVENTION

This invention relates to diagnostic instruments and in particular provides an instrument for testing or assessing dermatomes in peripheral neurological examinations.

A dermatome is an area of skin delimited in extent by the supply of sensory fibres from a single spinal nerve. A diagnostic or investigative analysis of dermatomes can therefore reveal to the skilled medical practitioner information relating to certain aspects of the condition of the patient's spinal cord.

According to the present invention a dermatome testing instrument comprises a barrel member and a probe member, in which the probe member is slidable longitudinally relative to and preferably within the barrel member and is resiliently biased towards a position in which the tip region of the probe member extends from the barrel member.

The tip of the probe member is preferably formed to a rounded point which is fine enough to permit of precise application to particular skin areas or dermatomes without being so sharp as to cause undue discomfort to the patient.

In use, the barrel member is held in the hand of the medical practitioner and the tip of the probe member is tapped gently and repeatedly against the patient's skin, and the response or reaction of the patient is taken into account by the practitioner in arriving at an opinion or diagnosis. The resilience of the probe member has the effect of cushioning the tapping, whereby the force exerted by the instrument, or the sensation experienced by the patient, is primarily a function of the strength of the resilient biassing of the probe member and only secondarily, within reasonable limits, of the power exerted by the medical practitioner. The tapping force on the patient's skin is therefore rendered more consistent, and diagnosis rendered more precise, than with non-resilient testing instruments.

Optionally, the probe member may be fully retractable within the barrel member, for transport or storage without damage being caused to or by the tip. Conveniently, the instrument is similar in size to a pen, whereby it may be carried in the pocket, and may be formed with or include a clip and/or a removable cap which may itself include a tongue extending longitudinally from the skirt edge thereof and which forms a clip in conjunction with the external surface of the barrel member.

Preferably the barrel member and probe member are formed from metallic materials and the barrel member in particular may be of any desired shape or formed with any pattern or ornamental features for functional or aesthetic purposes.

BRIEF DESCRIPTION OF THE DRAWING

Embodiments of the invention will now be described by way of example with reference to the accompanying drawing, which is an axial cross-sectional view of a dermatome testing instrument according to the invention.

DESCRIPTION OF THE PREFERRED EMBODIMENT

Figure 1:
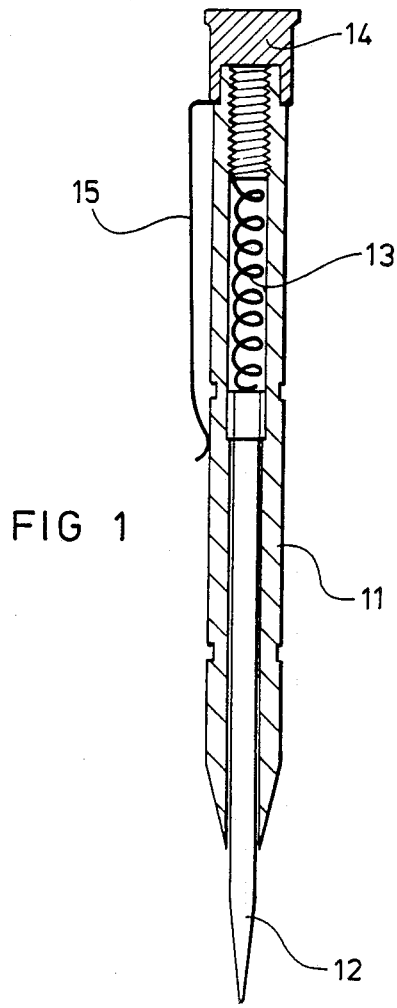

In the drawing, the instrument consists of a barrel member 11 and a probe member 12. The probe member is resiliently biassed towards an outer extended position (as shown) by means of a helical spring 13 located within the barrel. The barrel is equipped with a plastics end closure cap 14 and a pocket clip 15.

I claim:

1. A method of examination of dermatomes for diagnostic purposes, the method comprising:
   providing a dermatome testing instrument comprising a barrel member and a probe member, in which the probe member is slidable longitudinally relative to the barrel member and is resiliently biassed towards a position in which a tip region of the probe member extends from the barrel member, said probe member terminating distally in a tip formed to a rounded point;
   lightly tapping the probe member against the skin of a patient; and
   evaluating the response or reaction of the patient, the sensation experienced by that patient being primarily a function of the strength of the resilient biassing of the probe member in combination with the weight of the instrument.

* * * * *